United States Patent
Nichols et al.

(10) Patent No.: US 8,759,084 B2
(45) Date of Patent: Jun. 24, 2014

(54) SELF-STERILIZING AUTOMATED INCUBATOR

(76) Inventors: Michael J. Nichols, Brookline, MA (US); Louis J. Guarracina, Newburyport, MA (US)

( * ) Notice: Subject to any disclaimer, the term of this patent is extended or adjusted under 35 U.S.C. 154(b) by 490 days.

(21) Appl. No.: 13/011,477

(22) Filed: Jan. 21, 2011

(65) Prior Publication Data

US 2011/0183411 A1    Jul. 28, 2011

Related U.S. Application Data

(60) Provisional application No. 61/297,569, filed on Jan. 22, 2010.

(51) Int. Cl.
| | |
|---|---|
| C12M 1/00 | (2006.01) |
| C12M 3/00 | (2006.01) |
| B01L 1/00 | (2006.01) |
| B01L 7/00 | (2006.01) |

(52) U.S. Cl.
CPC .............. C12M 41/14 (2013.01); C12M 23/48 (2013.01); B01L 1/00 (2013.01); B01L 7/00 (2013.01)
USPC .......................................... 435/303.1; 422/1

(58) Field of Classification Search
CPC ......... C12M 41/14; C12M 23/48; B01L 7/52; B01L 7/00; B01L 2300/0829
USPC .......................................... 435/303.1; 422/1
See application file for complete search history.

(56) References Cited

U.S. PATENT DOCUMENTS

| | | |
|---|---|---|
| 40,106 A | 9/1863 | Jones et al. |
| 1,468,108 A | 4/1921 | Hodges |
| 1,549,467 A | 8/1925 | Dumond et al. |
| 1,908,928 A | 5/1933 | Stein |
| 2,044,518 A | 6/1936 | Thorsetensen |
| 2,091,394 A | 8/1937 | Park |
| 2,130,617 A | 9/1938 | Dockham |
| 2,470,956 A | 5/1949 | Savidge |
| 2,624,650 A | 1/1953 | Perales |
| 3,302,804 A | 2/1967 | Harris |
| 3,512,859 A | 5/1970 | Barroero |

(Continued)

FOREIGN PATENT DOCUMENTS

| | | |
|---|---|---|
| CH | 689253 A5 | 1/1999 |
| CH | 690645 A5 | 11/2000 |

(Continued)

OTHER PUBLICATIONS

Baharlou, International Application No. PCT/US2011/022171, International Preliminary Report on Patentability, HRB-0015-PCT, Aug. 2, 2012, 7 pages.

(Continued)

*Primary Examiner* — Michael Hobbs
(74) *Attorney, Agent, or Firm* — Hoffman Warnick LLC

(57) ABSTRACT

A method and system for self-sterilizing an automated incubator is disclosed. The internal temperature of the automated incubator is elevated by forcing hot air to flow into the internal incubation chamber, wherein all mechanics and electronics associated with the automated plate mover are outside the internal incubation chamber. During sterilization, the heating system of the automated incubator will force hot air to flow over the internal surfaces of the incubator, thereby reducing contaminating microorganism resistance by inducing dehydration.

21 Claims, 9 Drawing Sheets

(56) References Cited

U.S. PATENT DOCUMENTS

| | | | |
|---|---|---|---|
| 3,984,942 A | 10/1976 | Schroth | |
| 4,118,280 A | 10/1978 | Charles et al. | |
| 4,250,266 A | 2/1981 | Wade | |
| 4,261,808 A | 4/1981 | Walter | |
| 4,336,329 A * | 6/1982 | Hesse et al. | 435/3 |
| 4,371,175 A | 2/1983 | Van Dyk, Jr. et al. | |
| 4,426,267 A | 1/1984 | Munz et al. | |
| 4,477,112 A | 10/1984 | Schulke | |
| 4,498,603 A | 2/1985 | Wittenborg | |
| 4,625,867 A | 12/1986 | Guibert | |
| 4,669,938 A | 6/1987 | Hayward | |
| 4,681,504 A | 7/1987 | Welch, Sr. | |
| 4,709,815 A | 12/1987 | Price et al. | |
| 4,734,005 A | 3/1988 | Blumberg | |
| 4,770,590 A | 9/1988 | Hugues et al. | |
| 4,789,209 A | 12/1988 | Teranishi | |
| 4,820,106 A | 4/1989 | Walde et al. | |
| 4,846,619 A | 7/1989 | Crabtree et al. | |
| 4,867,629 A | 9/1989 | Iwasawa et al. | |
| 4,871,676 A | 10/1989 | Yamada | |
| 4,907,889 A | 3/1990 | Simone | |
| 4,923,816 A | 5/1990 | Heeg et al. | |
| 4,952,108 A | 8/1990 | Weigand et al. | |
| 5,059,079 A | 10/1991 | Foulke et al. | |
| 5,061,296 A | 10/1991 | Sengpiel et al. | |
| 5,112,641 A | 5/1992 | Harada et al. | |
| 5,133,635 A | 7/1992 | Malin et al. | |
| 5,149,654 A | 9/1992 | Gross et al. | |
| 5,177,514 A | 1/1993 | Ushijima et al. | |
| 5,244,270 A | 9/1993 | Parker | |
| 5,263,425 A | 11/1993 | Koenig | |
| 5,266,777 A | 11/1993 | Oppawsky et al. | |
| 5,285,333 A | 2/1994 | Barr et al. | |
| 5,303,034 A | 4/1994 | Carmichael et al. | |
| 5,336,030 A | 8/1994 | Ostwald et al. | |
| 5,364,222 A | 11/1994 | Akimoto et al. | |
| 5,380,137 A | 1/1995 | Wada | |
| 5,394,734 A * | 3/1995 | Wenger | 73/29.01 |
| 5,401,299 A | 3/1995 | Kroeger et al. | |
| 5,403,140 A | 4/1995 | Carmichael et al. | |
| 5,415,760 A * | 5/1995 | Hitomi et al. | 204/415 |
| 5,470,744 A | 11/1995 | Astle | |
| 5,542,964 A | 8/1996 | Kroeger et al. | |
| 5,546,315 A | 8/1996 | Kleinschnitz | |
| 5,645,391 A | 7/1997 | Ohsawa et al. | |
| 5,647,718 A | 7/1997 | Wiesler et al. | |
| 5,655,871 A | 8/1997 | Ishii et al. | |
| 5,664,254 A | 9/1997 | Ohkura et al. | |
| 5,686,301 A | 11/1997 | Falkenberg et al. | |
| 5,718,339 A | 2/1998 | Woodruff | |
| 5,730,316 A | 3/1998 | Falk | |
| 5,735,587 A | 4/1998 | Malin et al. | |
| 5,788,447 A | 8/1998 | Yonemitsu et al. | |
| 5,813,817 A | 9/1998 | Matsumiya et al. | |
| 5,813,819 A | 9/1998 | Ohsawa et al. | |
| 404,488 A | 1/1999 | Raimann | |
| 5,867,003 A | 2/1999 | Hashimoto et al. | |
| 5,890,703 A | 4/1999 | Kaus et al. | |
| 5,894,941 A | 4/1999 | Woodruff | |
| 6,029,828 A | 2/2000 | Robbins et al. | |
| 6,099,461 A | 8/2000 | Maresch et al. | |
| 6,120,119 A | 9/2000 | Jelinski et al. | |
| 6,129,428 A | 10/2000 | Helwig et al. | |
| 6,206,493 B1 | 3/2001 | Sanchex-Levin et al. | |
| 6,213,705 B1 | 4/2001 | Wilson | |
| 6,228,636 B1 | 5/2001 | Yahiro et al. | |
| 6,279,584 B1 | 8/2001 | Huffman | |
| 6,297,047 B1 | 10/2001 | Butts | |
| 6,324,853 B1 | 12/2001 | Kelly et al. | |
| 6,330,489 B1 | 12/2001 | Iwakawa | |
| 6,334,752 B1 | 1/2002 | Suzuki | |
| 6,397,620 B1 | 6/2002 | Kelly et al. | |
| 6,450,598 B1 | 9/2002 | Hanel | |
| 6,478,524 B1 | 11/2002 | Malin | |
| 6,503,751 B2 * | 1/2003 | Hugh | 435/303.1 |
| 6,518,059 B1 | 2/2003 | Butts | |
| 6,523,917 B2 | 2/2003 | Twellmann | |
| 6,534,014 B1 | 3/2003 | Mainquist et al. | |
| 6,536,859 B1 | 3/2003 | Bathe | |
| 6,568,770 B2 | 5/2003 | Gonska et al. | |
| 6,573,198 B2 | 6/2003 | Boonstra et al. | |
| 6,579,052 B1 | 6/2003 | Bonora et al. | |
| 6,582,174 B1 | 6/2003 | Hayashi | |
| 6,632,654 B1 | 10/2003 | Gebrian et al. | |
| 6,643,565 B2 | 11/2003 | Manes et al. | |
| 6,685,884 B2 | 2/2004 | Stylli et al. | |
| 6,690,993 B2 | 2/2004 | Foulke et al. | |
| 6,722,837 B2 | 4/2004 | Inui | |
| 6,752,479 B2 | 6/2004 | Ferger et al. | |
| 493,478 A1 | 7/2004 | Treadwell et al. | |
| 6,761,262 B2 | 7/2004 | Hertz et al. | |
| 6,840,255 B2 | 1/2005 | Buckner | |
| 6,846,146 B2 | 1/2005 | Inui | |
| 6,889,119 B2 | 5/2005 | Riff et al. | |
| 7,013,197 B2 | 3/2006 | Melching et al. | |
| 7,013,198 B2 | 3/2006 | Haas | |
| 7,028,913 B2 | 4/2006 | Reinhardt et al. | |
| 7,053,373 B1 | 5/2006 | Cleary | |
| 7,093,708 B2 | 8/2006 | Hertz et al. | |
| 7,096,091 B2 | 8/2006 | Haas et al. | |
| 7,100,396 B2 | 9/2006 | Melching et al. | |
| 7,137,770 B2 | 11/2006 | Ueda | |
| 7,152,664 B2 | 12/2006 | Kauschke et al. | |
| 7,195,737 B2 | 3/2007 | Itoh | |
| 7,214,022 B2 | 5/2007 | Melching | |
| 7,267,795 B2 | 9/2007 | Ammann et al. | |
| 7,311,435 B2 | 12/2007 | Heeg et al. | |
| 7,314,341 B2 | 1/2008 | Malin | |
| 7,326,565 B2 | 2/2008 | Yokoi et al. | |
| 7,329,394 B2 | 2/2008 | Weselak et al. | |
| 7,349,175 B2 | 3/2008 | McIntosh et al. | |
| 7,374,391 B2 | 5/2008 | Rice et al. | |
| 7,395,133 B2 | 7/2008 | Lowe | |
| 7,494,623 B2 | 2/2009 | Tansey, III et al. | |
| 7,510,362 B2 | 3/2009 | Malin | |
| 7,544,329 B2 | 6/2009 | Malin | |
| 7,556,779 B2 | 7/2009 | Melching et al. | |
| 7,578,097 B2 | 8/2009 | Dondlinger et al. | |
| 7,587,952 B2 | 9/2009 | Dale et al. | |
| 7,596,251 B2 | 9/2009 | Affleck et al. | |
| 2001/0035058 A1 * | 11/2001 | Wanek et al. | 73/865.6 |
| 2002/0018705 A1 | 2/2002 | Kawaguchi | |
| 2002/0050153 A1 | 5/2002 | Schultz et al. | |
| 2002/0163283 A1 | 11/2002 | Ferger | |
| 2003/0044262 A1 | 3/2003 | Inui | |
| 2003/0085230 A1 | 5/2003 | Hessler | |
| 2004/0216478 A1 | 11/2004 | Melching et al. | |
| 2004/0236463 A1 | 11/2004 | Weselak et al. | |
| 2004/0256963 A1 | 12/2004 | Affleck et al. | |
| 2005/0084420 A1 | 4/2005 | Osawa et al. | |
| 2005/0186054 A1 | 8/2005 | Inui | |
| 2005/0244306 A1 | 11/2005 | Stahl et al. | |
| 2006/0013730 A1 | 1/2006 | Pollock et al. | |
| 2006/0017357 A1 | 1/2006 | Riling et al. | |
| 2006/0018791 A1 | 1/2006 | Riling et al. | |
| 2006/0018802 A1 | 1/2006 | Greenway, Jr. et al. | |
| 2006/0018996 A1 | 1/2006 | Pollock et al. | |
| 2006/0028802 A1 | 2/2006 | Shaw et al. | |
| 2006/0182551 A1 | 8/2006 | Suess | |
| 2006/0270027 A1 | 11/2006 | Shaw et al. | |
| 2006/0279174 A1 * | 12/2006 | Oliver et al. | 310/338 |
| 2007/0041814 A1 * | 2/2007 | Lowe | 414/273 |
| 2007/0059205 A1 | 3/2007 | Ganz et al. | |
| 2007/0172396 A1 | 7/2007 | Neeper et al. | |
| 2008/0023417 A1 | 1/2008 | Yamamoto | |
| 2008/0044266 A1 | 2/2008 | Neeper et al. | |
| 2008/0116887 A1 | 5/2008 | Rogers | |
| 2008/0286086 A1 | 11/2008 | Fink et al. | |
| 2009/0029450 A1 | 1/2009 | Nakamura et al. | |
| 2009/0094909 A1 | 4/2009 | Cantrell | |
| 2009/0129014 A1 | 5/2009 | Larsen et al. | |

(56) References Cited

U.S. PATENT DOCUMENTS

| | | |
|---|---|---|
| 2009/0130749 A1 | 5/2009 | Ammann et al. |
| 2009/0247417 A1 | 10/2009 | Haas et al. |

FOREIGN PATENT DOCUMENTS

| | | |
|---|---|---|
| CH | 690962 A5 | 3/2001 |
| CH | 696326 A5 | 4/2007 |
| DE | 4229325 C2 | 12/1995 |
| DE | 19512531 C1 | 6/1996 |
| DE | 19537774 C2 | 9/1996 |
| DE | 19546542 C1 | 5/1997 |
| DE | 19816962 C1 | 10/1999 |
| DE | 19756510 C1 | 2/2000 |
| DE | 20022684 U1 | 3/2002 |
| DE | 20022900 U1 | 8/2002 |
| DE | 10114684 C2 | 10/2003 |
| DE | 20220550 U1 | 1/2004 |
| DE | 20220551 U1 | 1/2004 |
| DE | 10154663 B4 | 2/2004 |
| DE | 10304171 B4 | 2/2005 |
| DE | 10261995 B4 | 11/2005 |
| DE | 10161903 B4 | 5/2006 |
| DE | 102004010934 B4 | 8/2006 |
| DE | 19724133 B4 | 2/2007 |
| DE | 10303736 B4 | 5/2007 |
| DE | 10304012 B4 | 5/2007 |
| DE | 102005012373 B4 | 11/2007 |
| DE | 202008013492 U1 | 1/2009 |
| EP | 0598269 B1 | 11/1993 |
| EP | 0725133 B1 | 9/1995 |
| EP | 0808657 B1 | 4/1997 |
| EP | 1074488 B1 | 9/2002 |
| EP | 0913199 B1 | 1/2003 |
| EP | 1211197 B1 | 2/2003 |
| EP | 0829712 B1 | 5/2004 |
| EP | 1471138 A1 | 10/2004 |
| EP | 1322987 B1 | 8/2005 |
| EP | 0943676 B1 | 12/2005 |
| EP | 0923946 B1 | 3/2006 |
| EP | 1469944 B1 | 5/2006 |
| EP | 1155743 B1 | 9/2006 |
| EP | 1308504 B1 | 1/2007 |
| EP | 1445307 B1 | 7/2007 |
| EP | 1354028 B1 | 9/2007 |
| EP | 1443100 B1 | 9/2007 |
| EP | 0853657 B1 | 12/2007 |
| EP | 1634945 B1 | 2/2008 |
| EP | 1231258 B1 | 3/2008 |
| EP | 1721964 B1 | 5/2008 |
| EP | 1944358 A1 | 7/2008 |
| EP | 1552888 B1 | 1/2010 |
| EP | 1897935 B1 | 1/2010 |
| JP | 59186808 A | 10/1984 |
| JP | 61127506 A | 6/1986 |
| JP | 61131845 A | 6/1986 |
| JP | 61155108 A | 7/1986 |
| JP | 63314843 A | 12/1988 |
| JP | 1187283 A | 7/1989 |
| JP | 1308302 A | 12/1989 |
| JP | 4256603 A | 9/1992 |
| JP | 4277105 A | 10/1992 |
| JP | 4292312 A | 10/1992 |
| JP | 5198658 A | 8/1993 |
| JP | 5201505 A | 8/1993 |
| JP | 5262409 A | 10/1993 |
| JP | 6061331 A | 3/1994 |
| JP | 7010225 A | 1/1995 |
| JP | 2008054690 | 3/2008 |
| WO | 9419821 A1 | 9/1994 |
| WO | 9805753 A1 | 2/1998 |
| WO | 2005093038 A1 | 10/2005 |
| WO | 2008061137 A2 | 5/2008 |

OTHER PUBLICATIONS

Botella, PCT/US2011/022171, "PCT Notification of Transmittal of the International Search Report and Written Opinion of the International Searching Authority, or the Declaration", Apr. 15, 2011, 1 page.

Fischer, PCT/US2011/022171, "PCT International Search Report", Apr. 15, 2011, 4 pages.

Fischer, PCT/US2011/022171, PCT Written Opinion of the International Searching Authority, Apr. 15, 2011, 6 pages.

European Application No. 11 701 444.9-1356, Examination Report dated Mar. 19, 2014.

* cited by examiner

SELF-STERILIZING AUTOMATED INCUBATOR

This application claims the benefit of U.S. Provisional Application Ser. No. 61/297,569 filed on Jan. 22, 2010, and entitled "SELF-STERILIZING AUTOMATED INCUBATOR", which is incorporated by reference herein in its entirety.

TECHNICAL FIELD

Embodiments of the invention relate to a self-sterilizing automated incubator designed to allow dry heat sterilization in an automated incubator.

BACKGROUND

Contamination control and elimination is an important facet of cell culture efforts. Unwanted bacterial, viral or spore populations can easily ruin cell-based experiments common in biological and pharmaceutical research, and these populations can sometimes be notoriously difficult to detect and eliminate. Three principal methods of decontamination or sterilization have been used over the last century: dry heat, moist heat, and chemical.

Dry heat sterilization generally involves subjecting potentially contaminated items to a temperature of 120-160° C. for a period of one to two hours, at low relative humidity. This method of sterilization is effective at sterilizing items with good heat conductivity, such as metal parts, glassware, and the like.

Moist heat sterilization, on the other hand, can be performed in 20-30 minutes at a somewhat lower temperature than dry heat sterilization. However, it also requires steam and a pressure of 15-20 psi. This method was quickly adopted by hospitals because the pressurized steam penetrates wrapped instruments and packaged items much more quickly than dry heat.

The third method of decontamination involves spraying or wiping toxic chemicals onto potentially contaminated surfaces. This method is generally reserved for decontamination of items that are too large to put into a sterilization oven, or that contain sensitive electronics or other equipment that cannot survive a heat sterilization cycle.

Incubators have been used in cell culture and other laboratory applications for many years. More recently, automated incubators have been developed for use in automated laboratory robotic systems. Objects to be incubated (e.g., microtiter plates), instead of being placed in the incubator by hand, are handed off to a nest somewhere on the external surface of the automated incubator by a robot, upon which the incubator's automated object handling mechanism will move the object inside the incubation chamber to an unoccupied storage location. Reversing these steps causes the incubator to output the given object and present it to the robot.

Historically, both automated and non-automated (manual) incubators have been decontaminated by a combination of methods. Some laboratories may sterilize objects that can be removed from the internal chamber of the incubator, such as racks, shelves, or stackers, and autoclave (moist heat) or dry heat sterilize these pieces. Then, the internal surfaces of the incubator itself may be wiped down with toxic chemicals. Such a process is time-consuming, and the use of contamination-killing chemicals poses a certain danger to personnel and is avoided when possible.

Although cell incubators typically reach a maximum possible temperature of 50° C., some manual incubators use higher temperatures (130-160° C.) in order to sterilize the internal incubation chamber with a dry heat method. This, however, has not been possible in automated incubators, because the mechanics and electronics associated with the automated object movers inside the internal incubation chamber could not withstand high temperatures.

SUMMARY

A first aspect includes an automated incubator including an internal incubation chamber and an automated plate mover, the automated incubator comprising: a heating system configured to force hot air into the internal incubation chamber of the automated incubator, wherein all mechanics and electronics associated with the automated plate mover are located outside the internal incubation chamber.

A second aspect includes a method for sterilizing an automated incubator including an internal incubation chamber and an automated plate mover, the method comprising: removing any plates in the internal incubation chamber; and forcing hot air to flow into the internal incubation chamber to elevate an internal temperature of the internal incubation chamber, wherein all mechanics and electronics associated with the automated plate mover are located outside the internal incubation chamber.

The advantages of this novel self-sterilizing automated incubator will be described in more detail below.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

The self-sterilizing automated incubator disclosed herein is designed to allow dry heat sterilization in an automated incubator. This is generally accomplished by locating all mechanics and electronics associated with the automated plate mover outside the internal incubation chamber, thereby preventing damage to the electronics from the high heat of the sterilization cycle.

Figure 1:
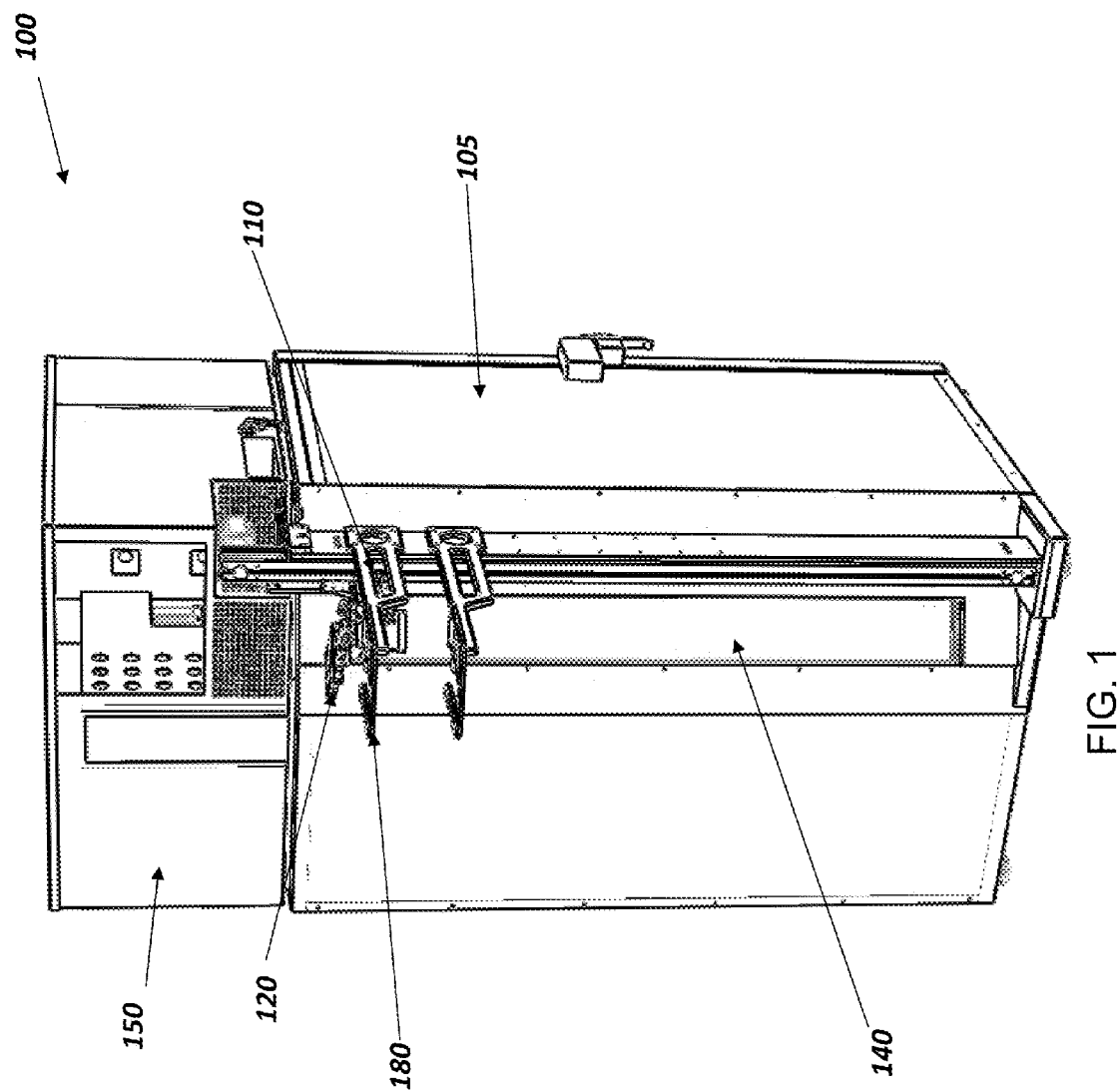
FIG. 1 shows a perspective view of a self-sterilizing automated incubator according to an embodiment of the invention.
Figure 2:
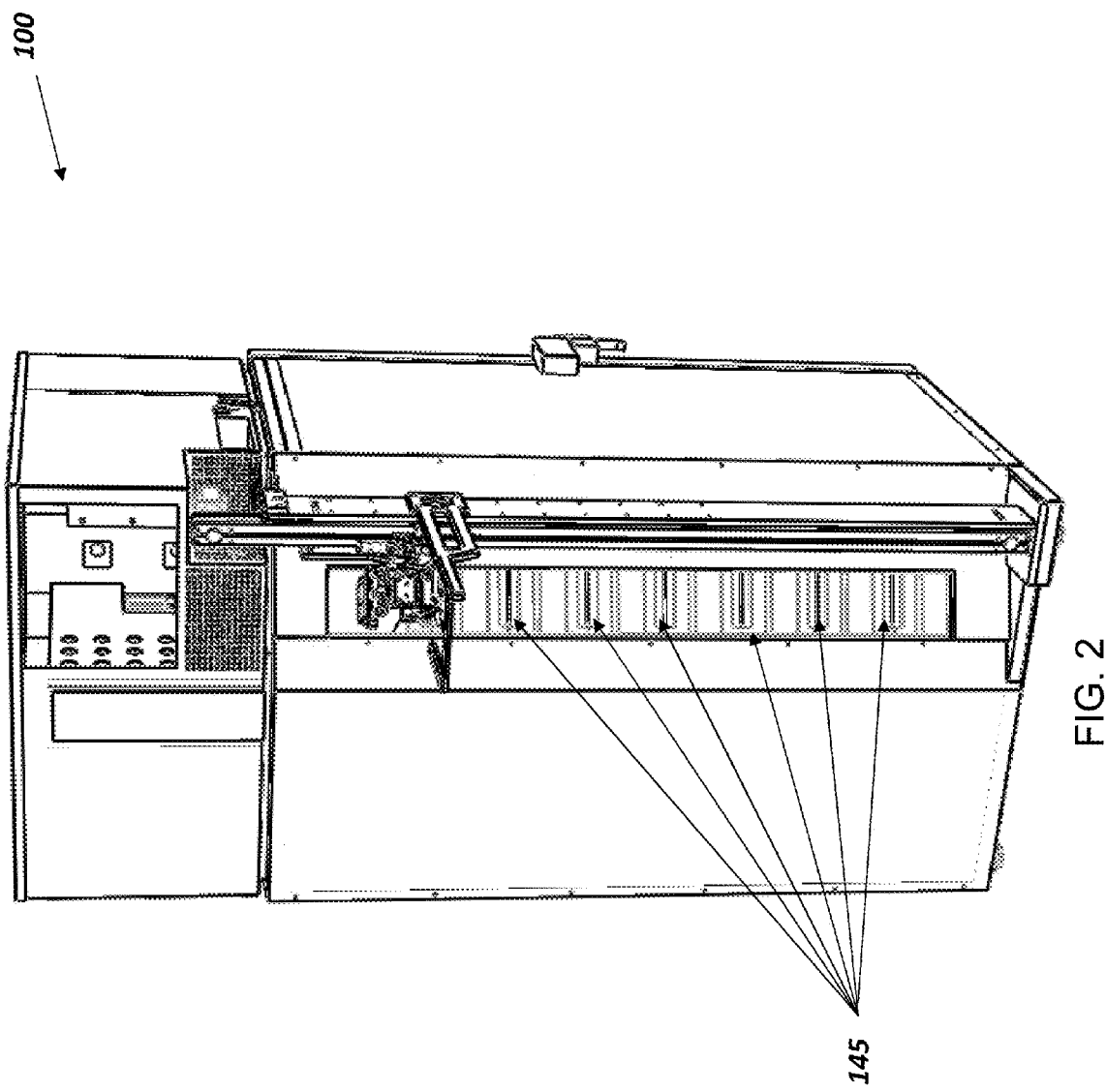
FIG. 2 shows a side perspective view of a self-sterilizing automated incubator with an outer door removed.
Figure 3:
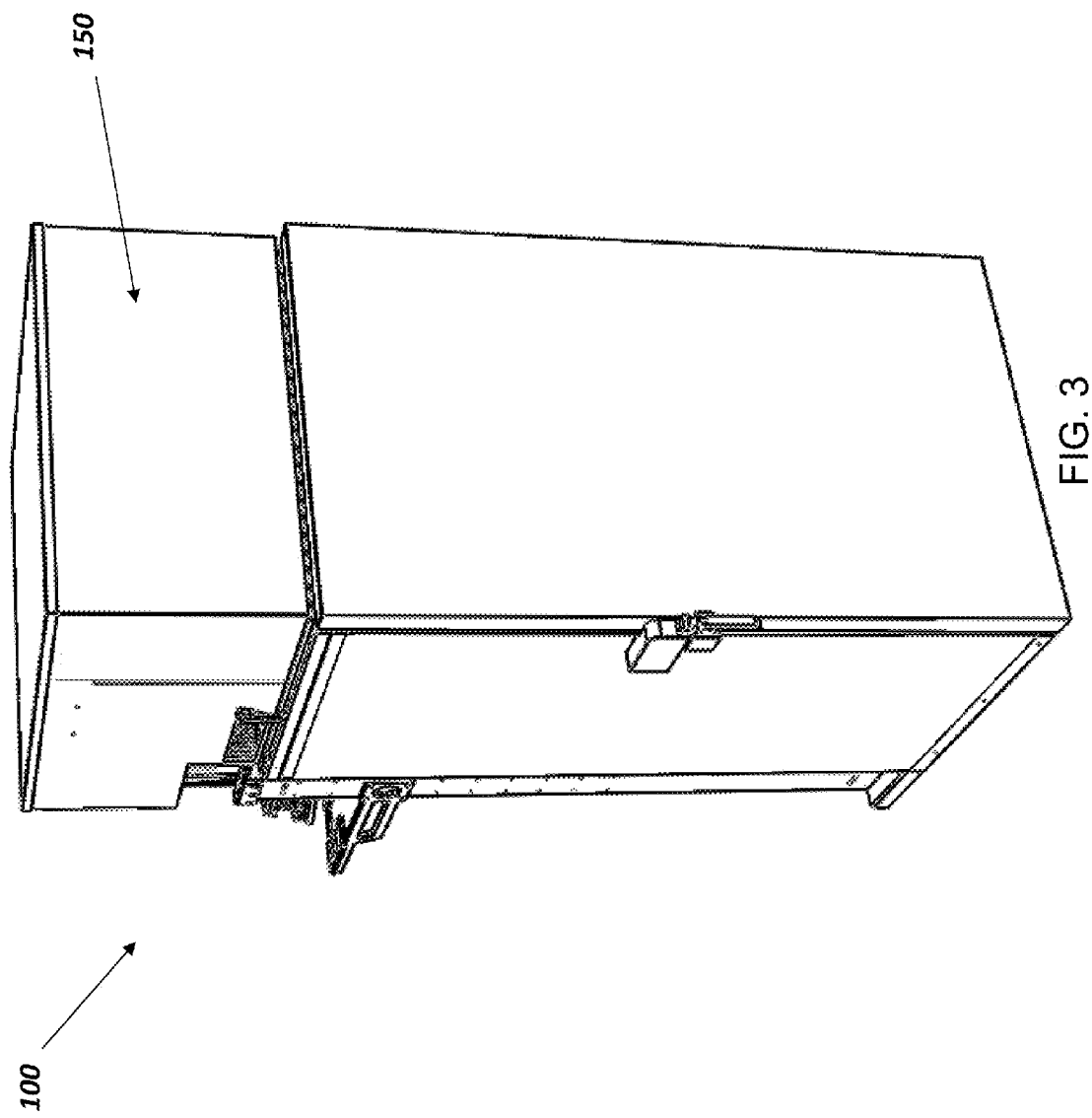
FIG. 3 shows another perspective view of a self-sterilizing automated incubator according to an embodiment of the invention
Figure 4:
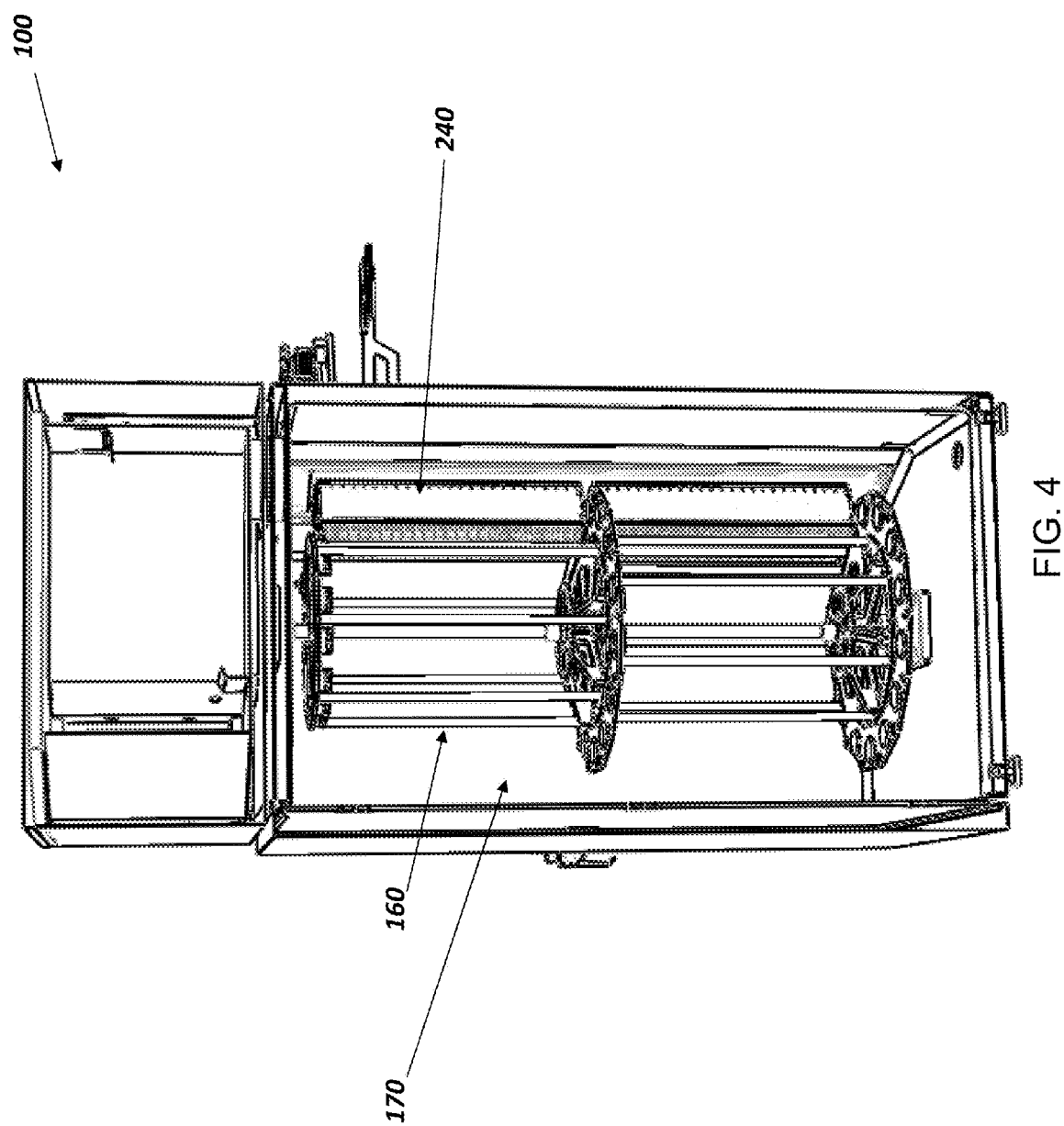
FIG. 4 shows a side view of an incubation chamber according to embodiments of the invention with the side removed exposing a carousel inside.
Figure 5:
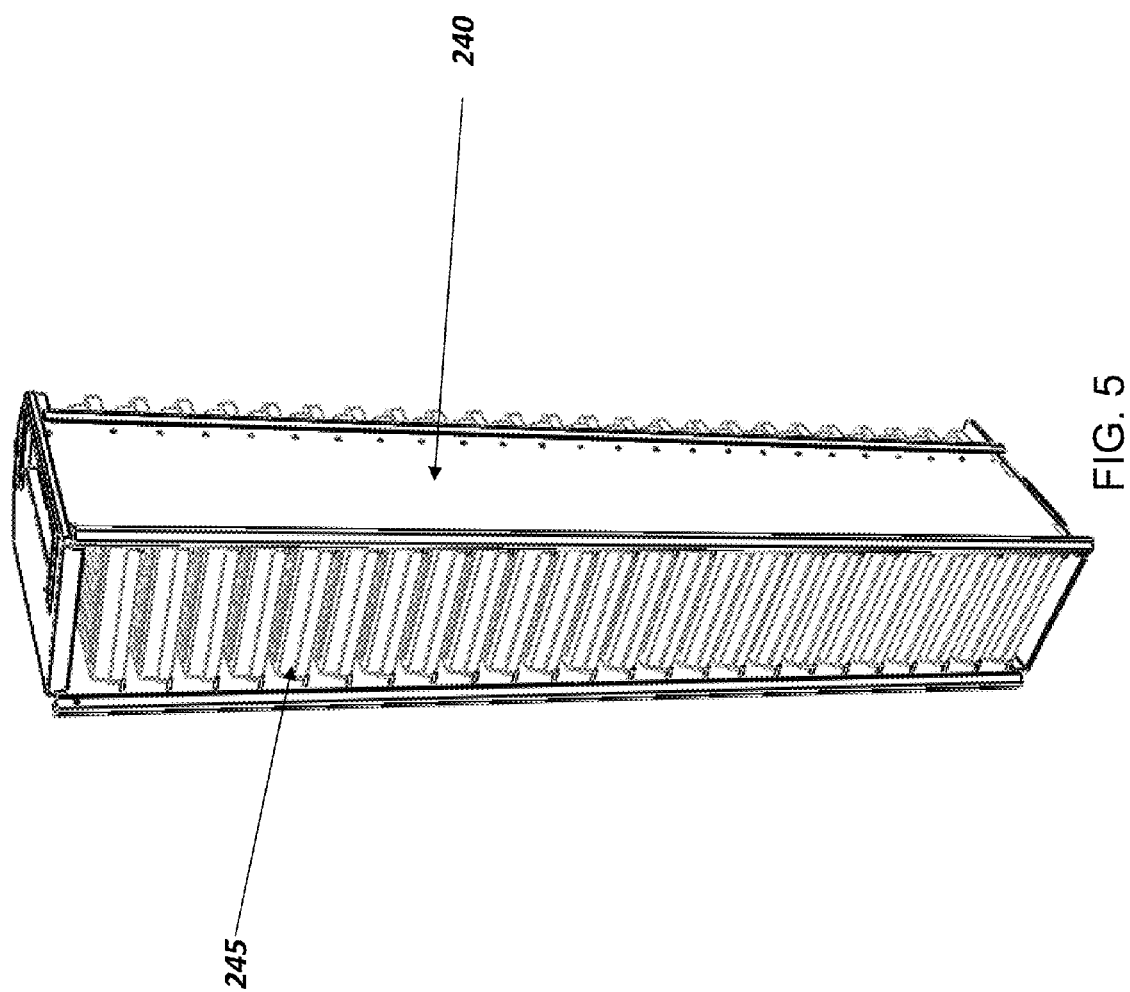
FIG. 5 shows a perspective view of a stacker used in an automated incubator.
Figure 6:
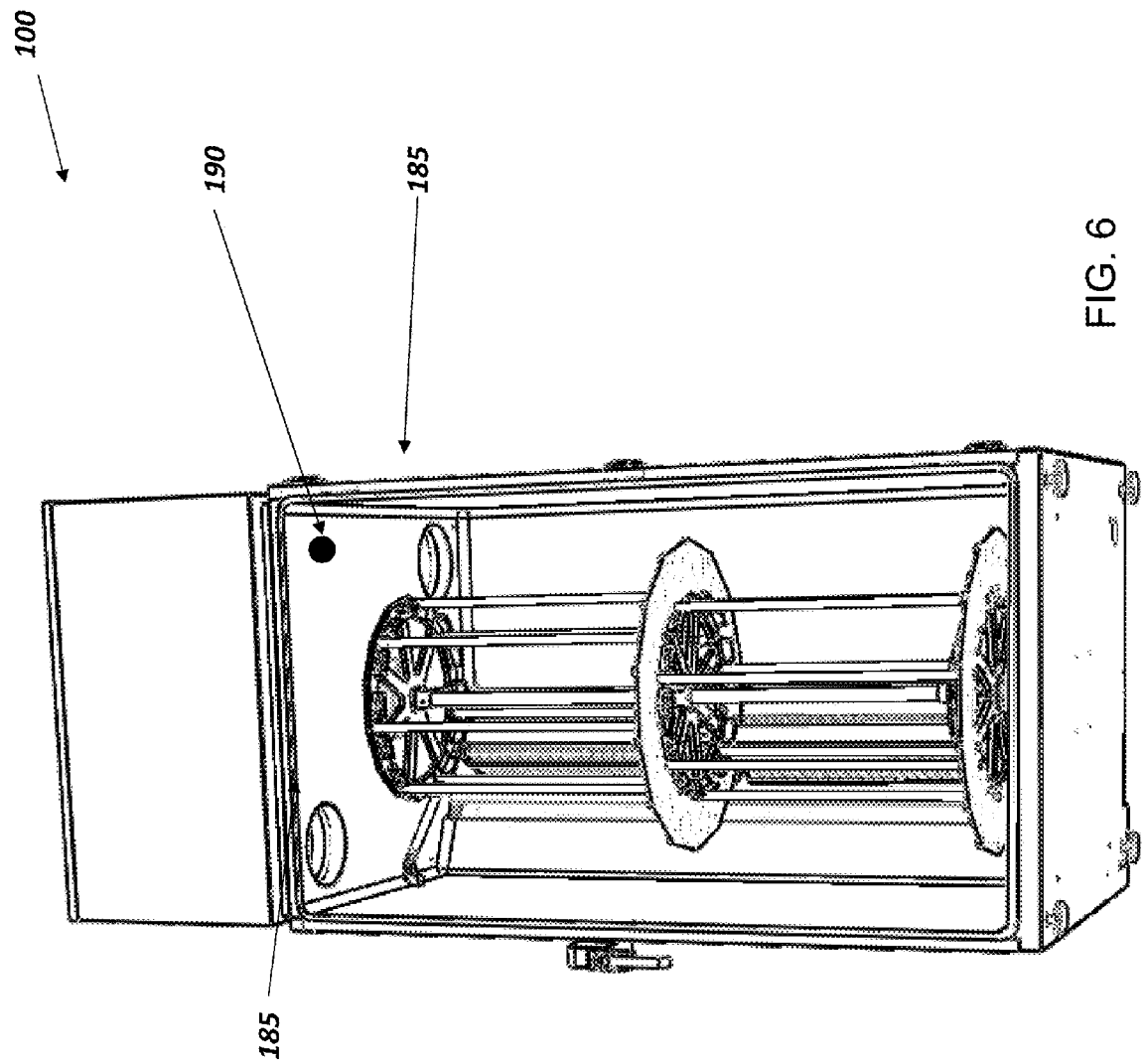
FIG. 6 shows a side view of an incubation chamber according to embodiments of the invention with the side removed exposing a carousel inside.
Figure 7:
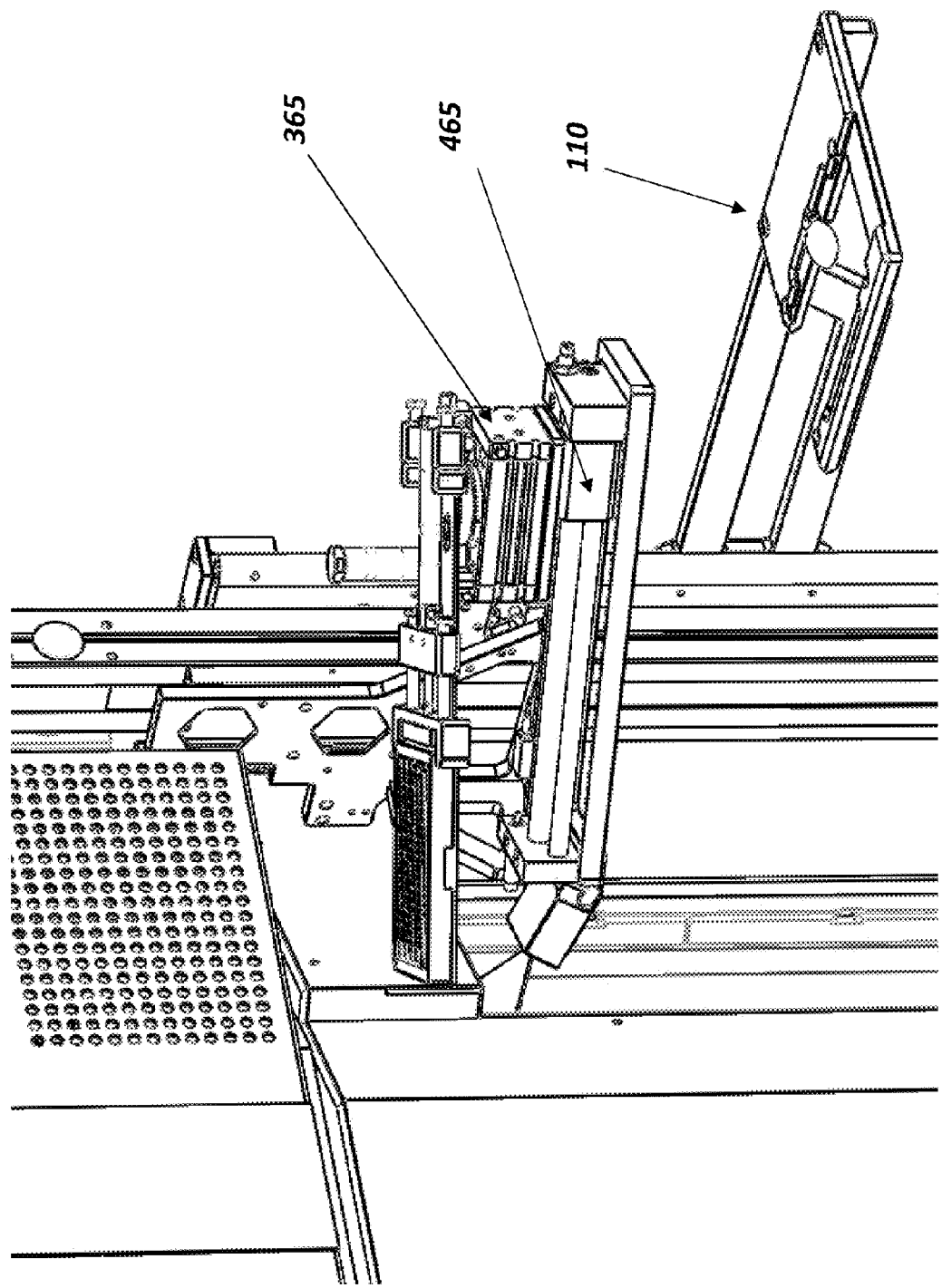
FIG. 7 shows a perspective view of the robotics used in an automated incubator according to embodiments of the invention.
Figure 8:
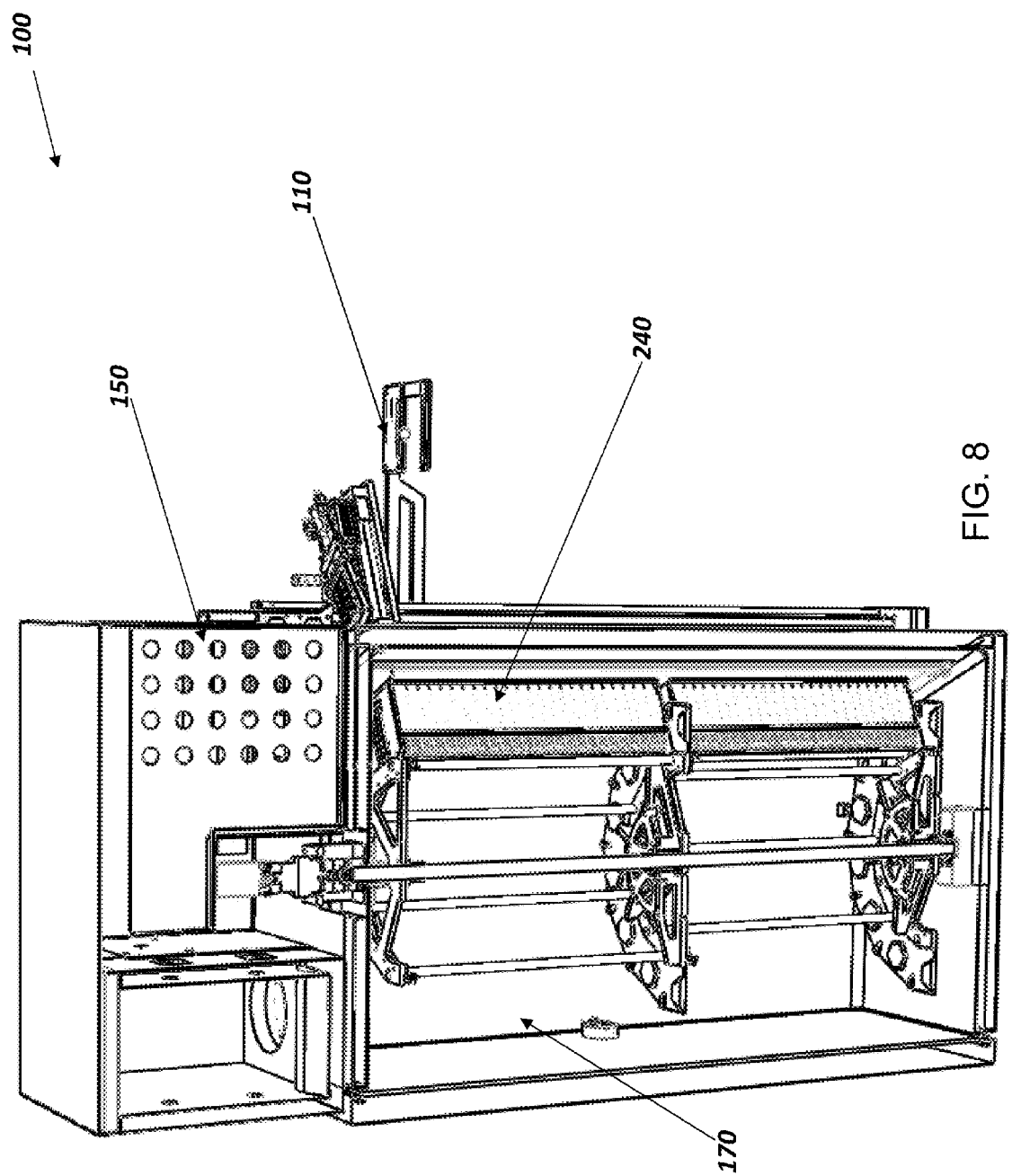
FIG. 8 shows a partial cut-out top perspective view of a self-sterilizing automated incubator according to embodiments of the invention.
Figure 9:
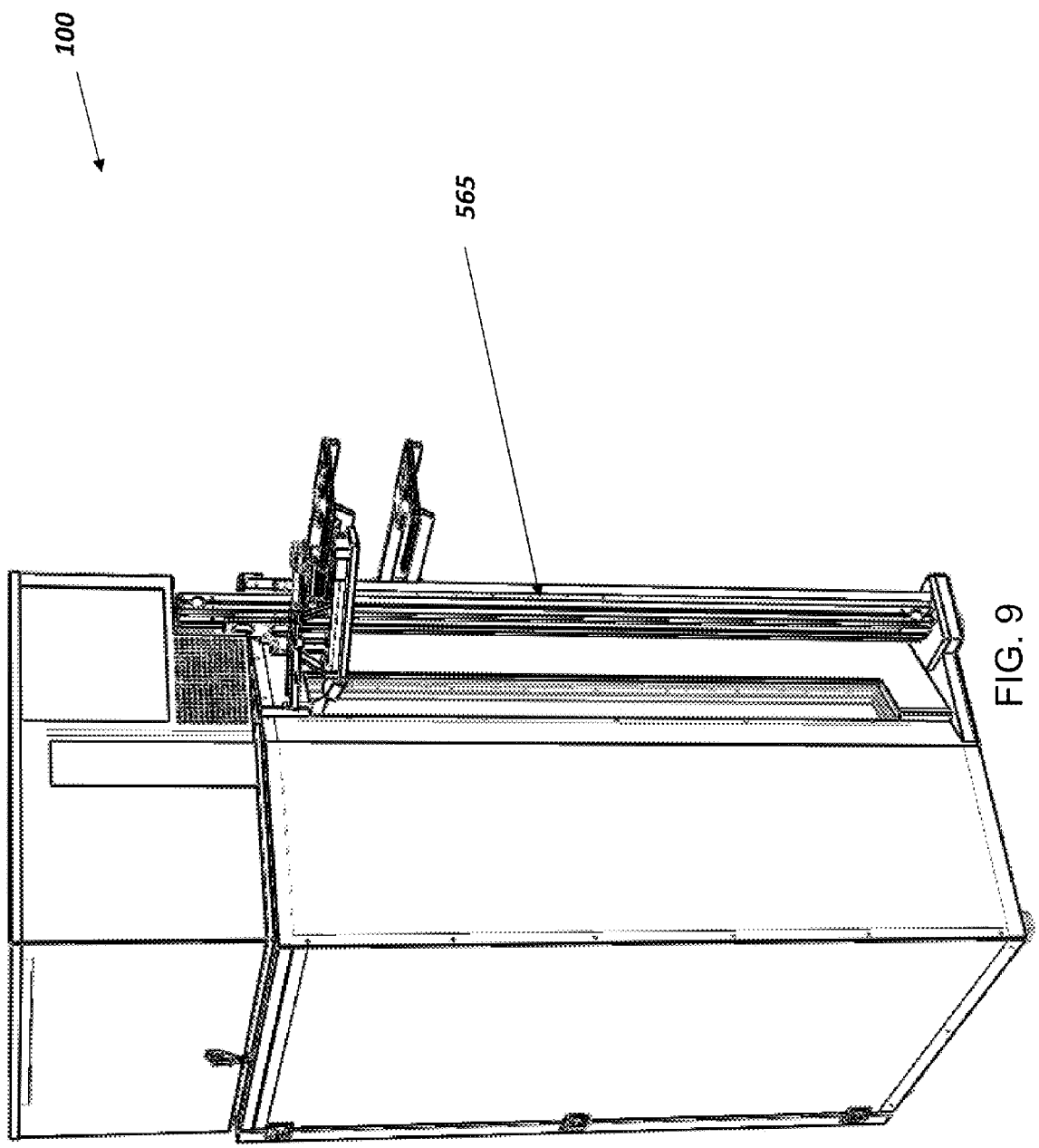
FIG. 9 shows a perspective view of a self-sterilizing automated incubator according to embodiments of the invention.

As shown in FIGS. 1-9, during typical operation integrated with an automated incubator system 100, plates to be incubated are placed onto the incubator's plate input/output nest 110 by the system's central robot (not shown). The integrated system's control software (not shown), located within housing 150, instructs the automated incubator 105 to place the plate 180 into a destination stacker 240 (FIG. 4) in the internal incubation chamber 170. All mechanics and electronics associated with the automated plate mover are located outside the internal incubation chamber 170 and may be located within housing 150. The plate carriage 120 moves into position underneath plate 180 in the input/output nest 110. The plate carriage 120 lifts plate 180 up out of the nest 110, then rotates plate 180 toward automated doors 140, 145. Robotic system 100 may include both an automated outer door 140 and automated inner doors 145, or may include only one automated door, for example, only outer door 140, without inner door(s) 145. The internal carousel 160 rotates to present the destination stacker 240 such that it is adjacent and aligned to the automated doors 140, 145. The outer automated outer door 140 opens, as well as one of the numerous automated inner doors 145 (if included), to expose the destination stacker 240. Destination stacker 240 includes microtiter plates 245. The plate carriage vertical axis 565 (FIG. 9) aligns plate 180 in the plate carriage 120 to the unoccupied destination position in the stacker, then the plate carriage horizontal axis 465 (FIG. 7) actuates to carry the plate 180 through the automated doors 140, 145 and into the correct stacker location. Plate carriage rotary axis 365 (FIG. 7) may also be used to carry plate 180 through automated doors 140, 145. Once the plate carriage 120 retracts out of the internal incubation chamber 170, both the automated inner door 145 and automated outer door 140 close.

Once the plate 180 is finished incubating, the integrated system's control software (not shown) will instruct the automated incubator 105 to retrieve the plate 180 and set it onto the plate input/output nest 110, upon which the system's central robot will pick up the plate 180 and move it to the next process step.

Periodically, the system operator will want to sterilize the internal incubation chamber 170. At such time, all plates 180 will be removed from the internal incubation chamber 170, and the automated incubator 105 will be set to perform a sterilization cycle. During the sterilization cycle, the internal temperature of the internal incubation chamber 170 will be elevated to approximately 130-180° C., for a period of approximately one to four hours, for example, for approximately three hours. During this time, the heating system, located within housing 150, will force hot air through inlets 185 to flow over the internal surfaces, reducing contaminating microorganism resistance by inducing dehydration. The empty stackers remain in the internal incubation chamber 170 so that they are sterilized in situ. In addition, the air handling system (not shown) is also sterilized.

In order to regulate the temperature inside the internal incubation chamber 170 during both incubation and sterilization, temperature sensors (not shown) are located inside the internal incubation chamber 170 to capture the internal temperature. The internal temperature data is sent to a controller, located within housing 150, which regulates the internal incubation chamber 170 to the appropriate temperature through the use of the heating system and a refrigeration system, both located within housing 150. High temperature failsafe controls are also included within housing 150 to ensure that the incubator will not overheat past a rated maximum temperature if the controller malfunctions.

In order to facilitate cell growth, the incubator controls humidity level in the internal incubation chamber 170. A common technique for achieving high humidity in cell incubators is placing an open pan of water at the bottom of a chamber. However, this can be a source of contamination. In order to minimize the opportunity for contaminating microorganisms to gain a foothold in internal incubation chamber 170, the automated incubator 105 according to embodiments of this invention includes a humidity sensor (not shown) inside the internal incubation chamber 170. The humidity sensor may be a digital capacitive sensor that measures the relative humidity value and sends this value to the controller. The controller, located within housing 150, then regulates the relative humidity within the internal incubation chamber when the relative humidity does not meet a threshold. In one embodiment, the controller can increase or decrease the relative humidity by regulating at least one atomizing nozzle 190. The atomizing nozzles 190 are regulated by opening and closing a valve that controls a supply of water to the inside of internal incubation chamber 170, e.g. a solenoid valve. This atomizing nozzle 190 atomizes water directly into the internal incubation chamber 170. The water pressure to the internal incubation chamber 170 may be between approximately 80 and 100 pounds per square-inch (psi). Demineralized, dionized, or single distilled water may be used. The resistance of the water may be between approximately 0.5 and 2.0 MΩ (mega ohms).

It is also understood that instead of, or in addition to, utilizing a water atomizer, the relative humidity can be regulated by introducing steam into the internal incubation chamber through the use of a submersible heater in a reservoir to boil water off into steam. For example, a reservoir can be provided at the base of internal incubation chamber 170. A submersible heater can be included in the reservoir. The controller in housing 150 can control the submersible heater such that it heats the water in reservoir at a desired temperature to control the rate that the water will boil off. Water can be introduced into the reservoir through any known means, for example, by using a container with a spring loaded cap. The container can be filled with water, then turned over so that the cap contacts a mechanism near the reservoir that triggers the spring loaded cap and allows water to flow into the reservoir.

One humidity sensor has a temperature operating range of approximately −40° C. to +150° C.; however, the humidity sensor can survive exposure to temperatures of approximately −75° C. to +200° C. Also, the humidity sensor can measure a humidity value between approximately 0 and 99% relative humidity (RH).

In addition to humidity, the automated incubator 105 according to embodiments of this invention also controls concentrations of carbon dioxide ($CO_2$) and nitrogen ($N_2$) levels within the internal incubation chamber 170.

In order to regulate the $CO_2$ concentration level in the internal incubation chamber 170, an infrared gas sensor (not shown) is located inside the internal incubation chamber 170 for measuring $CO_2$ concentrations. The infrared gas sensor uses the characteristic absorption of $CO_2$ to determine the concentration of $CO_2$ within the internal incubation chamber 170. The infrared gas sensor may include a single beam, dual wavelength silicon based transmitter. The measured values from this sensor are relayed to the controller, located within housing 150. A desired or pre-set $CO_2$ concentration level is maintained through the increasing (decreasing) of $CO_2$ into the internal incubation chamber. In one embodiment, a valve is located inside the internal incubation chamber 170 and the controller opens and closes the valve to control the increasing (decreasing) of $CO_2$ from a source thereof to a $CO_2$ port coupled by a valve to a source of $CO_2$ in order to control the $CO_2$ concentration when the $CO_2$ concentration does not meet a threshold. The pressure of gaseous $CO_2$ within the internal incubation chamber 170 may be between approximately 100 and 300 psi.

In order to regulate the $N_2$ concentration level in the internal incubation chamber 170, a micro fuel cell sensor (not shown) is located inside the internal incubation chamber 170 for measuring the $N_2$ concentration (between 0 to 100%). The micro fuel cell sensor has an operating temperature range of approximately 0° C. to 50° C. and can be calibrated with air. The micro fuel cell sensor relays the measured $N_2$ levels in the internal incubation chamber 170 to the controller, located within housing 150. In one embodiment, a valve is located inside the internal incubation chamber 170 and the controller opens and closes the valve to control the increasing (decreasing) of $N_2$ from a source thereof to a $N_2$ port coupled by a valve to a source of $N_2$ in order to control the $N_2$ concentration level when the $N_2$ concentration does not meet a threshold. The pressure of gaseous $N_2$ within the internal incubation chamber 170 may be approximately 100 psi.

Some incubators use copper-lined chambers in order to help reduce contamination, as copper quickly oxidizes any surface-borne microorganisms. The automated incubator according to embodiments of this invention uses mostly stainless steel in the interior, but other materials, such as copper, can be offered.

The foregoing description of various aspects of the invention has been presented for the purpose of illustration and description. It is not intended to be exhaustive or to limit the invention to the precise form disclosed, and obviously, many modifications and variations are possible. Such variations and modifications that may be apparent to one skilled in the art are intended to be included within the scope of the present invention as defined by the accompanying claims.

What is claimed is:

1. An automated incubator including an internal incubation chamber and an automated plate mover, the automated incubator comprising:
   a heating system configured to force hot air into the internal incubation chamber of the automated incubator, wherein all mechanics and electronics associated with the automated plate mover are located outside the internal incubation chamber,
   wherein the heating system forces sufficient hot air into the internal incubation chamber to raise an internal temperature of the internal incubation chamber to approximately 130-180° C., for a period of approximately one to four hours; and
   a housing connected with the internal incubation chamber, the housing including a controller programmed to regulate the internal temperature within the internal incubation chamber and a relative humidity within the internal incubation chamber by instructing the heating system to force sufficient hot air into the internal incubation chamber to raise the internal temperature of the internal incubation chamber to approximately 130-180° C., for the period of approximately one to four hours, wherein the controller is located outside of the internal incubation chamber.

2. The automated incubator of claim 1, further comprising a refrigeration system configured to force cold air into the internal incubation chamber of the automated incubator.

3. The automated incubator of claim 1, further comprising a temperature sensor within the internal incubation chamber configured to measure the internal temperature of the internal incubation chamber.

4. The automated incubator of claim 1, further comprising a humidity sensor within the internal incubation chamber configured to measure a relative humidity value within the chamber.

5. The automated incubator of claim 4, wherein the humidity sensor is a digital capacitive sensor.

6. The automated incubator of claim 5, further comprising at least one atomizing nozzle configured to increase the relative humidity within the internal incubation chamber by directly atomizing water into the internal incubation chamber.

7. The automated incubator of claim 6, wherein the at least one atomizing nozzle is regulated by opening and closing a valve that controls a supply of water.

8. The automated incubator of claim 1, further comprising a carbon dioxide ($CO_2$) sensor within the internal incubation chamber configured to measure a $CO_2$ concentration within the internal incubation chamber.

9. The automated incubator of claim 8, wherein the $CO_2$ sensor is an infrared gas sensor.

10. The automated incubator of claim 9, further comprising a $CO_2$ port coupled by a valve to a source of $CO_2$, the $CO_2$ port configured to increase the $CO_2$ concentration within the internal incubation chamber.

11. The automated incubator of claim 1, further comprising a nitrogen ($N_2$) sensor within the internal incubation chamber configured to measure an $N_2$ concentration within the internal incubation chamber.

12. The automated incubator of claim 11, wherein the $N_2$ sensor is a micro fuel cell sensor.

13. The automated incubator of claim 12, further comprising a $N_2$ port coupled by a valve to a source of $N_2$, the $N_2$ port configured to increase the $N_2$ concentration within the internal incubation chamber.

14. The automated incubator of claim 1, wherein the automated plate mover includes a plate carriage connected with the controller, wherein the automated incubator further includes:
    a destination stacker within the internal incubation chamber; and
    automated doors connected with the controller for opening and closing the internal incubation chamber,
    wherein the controller is further programmed to:
      instruct the automated doors to open; and
      instruct the plate carriage to place a plate into the destination stacker,
    wherein the plate carriage is external to the internal incubation chamber.

15. The automated incubator of claim 14, further comprising an internal carousel connected with the destination stacker within the internal incubation chamber, wherein the internal carousel is programmed to rotate to present the destination stacker such that it is adjacent and aligned with the automated doors.

16. The automated incubator of claim 15, wherein the controller is programmed to:
    instruct the plate carriage to remove all plates from the destination stacker;
    instruct the automated doors to close after the removal of all of the plates from the destination stacker; and
    instruct the heating system to force the hot air into the internal incubation chamber to raise the internal temperature of the internal incubation chamber to approximately 130-180° C., for the period of approximately one to four hours.

17. An automated incubator comprising:
an internal incubation chamber including a heating system configured to force hot air into the internal incubation chamber of the automated incubator;
a housing connected with the internal incubation chamber, the housing including a controller programmed to regulate the internal temperature within the internal incubation chamber and a relative humidity within the internal incubation chamber, wherein the controller is located outside of the internal incubation chamber;
a plate carriage connected with the controller;
a destination stacker within the internal incubation chamber; and
automated doors connected with the controller for opening and closing the internal incubation chamber,
wherein the controller is further programmed to:
instruct the automated doors to open; and
instruct the plate carriage to place a plate into the destination stacker,
wherein the plate carriage is external to the internal incubation chamber.

18. The automated incubator of claim 17, further comprising an internal carousel connected with the destination stacker within the internal incubation chamber, wherein the internal carousel is programmed to rotate to present the destination stacker such that it is adjacent and aligned with the automated doors.

19. The automated incubator of claim 18, wherein the controller is programmed to:
instruct the plate carriage to remove all plates from the destination stacker;
instruct the automated doors to close after the removal of all of the plates from the destination stacker; and
instruct the heating system to force the hot air into the internal incubation chamber to raise an internal temperature of the internal incubation chamber to approximately 130-180° C., for a period of approximately one to four hours.

20. An automated incubator comprising:
an internal incubation chamber including:
a heating system configured to force hot air into the internal incubation chamber of the automated incubator; and
a temperature sensor within the internal incubation chamber configured to measure the internal temperature of the internal incubation chamber;
a housing connected with the internal incubation chamber, the housing including a controller programmed to regulate the internal temperature within the internal incubation chamber and a relative humidity within the internal incubation chamber, wherein the controller is located outside of the internal incubation chamber;
a plate carriage connected with the controller;
a destination stacker within the internal incubation chamber;
automated doors connected with the controller for opening and closing the internal incubation chamber,
wherein the controller is further programmed to:
instruct the automated doors to open; and
instruct the plate carriage to place a plate into the destination stacker,
wherein the plate carriage is external to the internal incubation chamber; and
an internal carousel connected with the destination stacker within the internal incubation chamber, wherein the internal carousel is programmed to rotate to present the destination stacker such that it is adjacent and aligned with the automated doors.

21. The automated incubator of claim 20, wherein the controller is programmed to:
instruct the plate carriage to remove all plates from the destination stacker; instruct the automated doors to close after the removal of all of the plates from the destination stacker; and
instruct the heating system to force the hot air into the internal incubation chamber to raise the internal temperature of the internal incubation chamber to approximately 130-180° C., for a period of approximately one to four hours.

* * * * *